United States Patent

Mosimann

[11] 4,012,841
[45] Mar. 22, 1977

[54] DEVICE FOR FIXING A DENTAL DRILL INTO A ROTOR

[76] Inventor: David Mosimann, Chemin des Grillons 13-15, Bienne, Switzerland

[22] Filed: Sept. 23, 1975

[21] Appl. No.: 616,023

[30] Foreign Application Priority Data

Sept. 30, 1974 Switzerland .................. 013157/74

[52] U.S. Cl. .................................................. 32/27
[51] Int. Cl.² .......................................... A61C 1/10
[58] Field of Search .................. 32/27, 26; 279/23

[56] References Cited

UNITED STATES PATENTS

| | | | |
|---|---|---|---|
| 2,467,606 | 4/1949 | Young | 279/23 |
| 2,564,893 | 8/1951 | Gibbons | 279/23 |
| 2,570,570 | 10/1951 | Lee | 279/23 |

FOREIGN PATENTS OR APPLICATIONS 1,072,069  9/1954  France .................................. 32/27

*Primary Examiner*—Robert Peshock
*Attorney, Agent, or Firm*—Bacon & Thomas

[57] ABSTRACT

A holder for a dental drill is formed by a helical spring drivingly connected to a driven rotor. The normal internal diameter of the spring is slightly less than the diameter of the shank of the drill to be used. Axial insertion of the drill into one end of the spring causes the spring to compress in length and thus increase in diameter sufficiently to receive the drill shank and frictionally grip the same. Means are provided for expanding the spring to release the drill.

4 Claims, 5 Drawing Figures

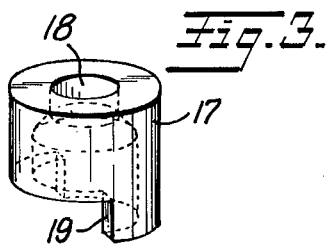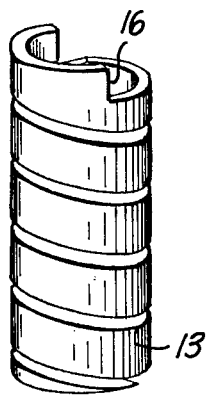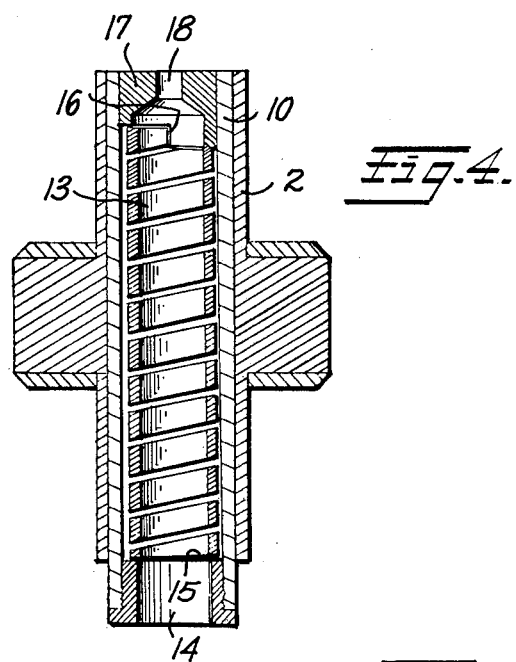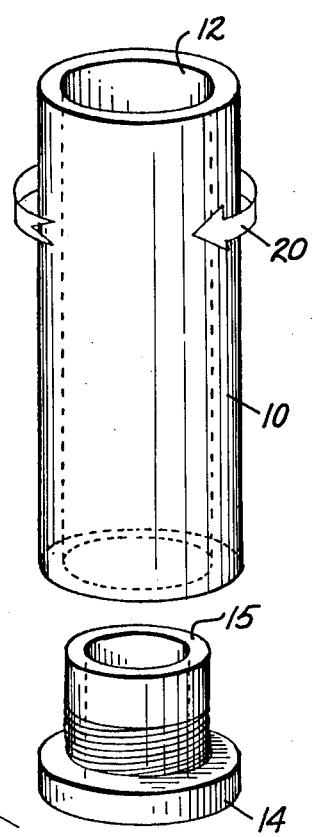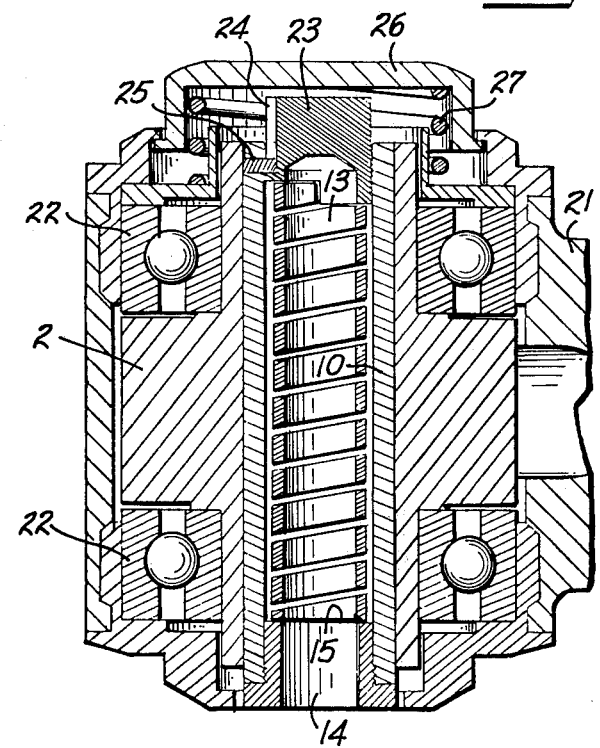

DEVICE FOR FIXING A DENTAL DRILL INTO A ROTOR

BACKGROUND OF THE INVENTION

This invention is in the field of dental tools and particularly dental drills.

As generally practiced at the present time removable drills are fixed in the rotors of high speed turbines by means of screw chucks or the like. Recently a device was proposed for applying resilient inward pressure to the drill to hold it in the rotor by friction, thus eliminating the need for screws and making it possible to insert the drill shank by simply pushing it axially without having to stop the rotor. A slotted sleeve was axially compressed by a helical spring or a body of rubber extending around the same but such devices applied maximum pressure only at a limited region intermediate the end of the drill shank, thus inducing excessive wear in that region and rendering it difficult to insert or remove a drill. The pressure necessary to insert the drill axially into those devices created the risk of breaking tungsten carbide drills or bending of diamond charged drills which are long and thin.

SUMMARY OF THE INVENTION

The object of the present invention is to largely remedy the aforementioned disadvantages and permit a simpler construction Another object of the invention is also to provide a drill holding means for a high speed dental turbine in which the drill can be inserted or withdrawn axially and is frictionally held by uniform frictional grip throughout substantially the entire length of the drill shank.

BRIEF DESCRIPTION OF THE DRAWINGS

FIG. 3 is an exploded view of the parts involved in one form of the present invention;

FIG. 4 is a sectional view through a dental turbine rotor having the parts of FIG. 3 installed therein; and FIG. 5 is a sectional view through the turbine head of a dental handpiece illustrating a second embodiment of the present invention.

DESCRIPTION OF THE PREFERRED EMBODIMENTS

Figure 1:
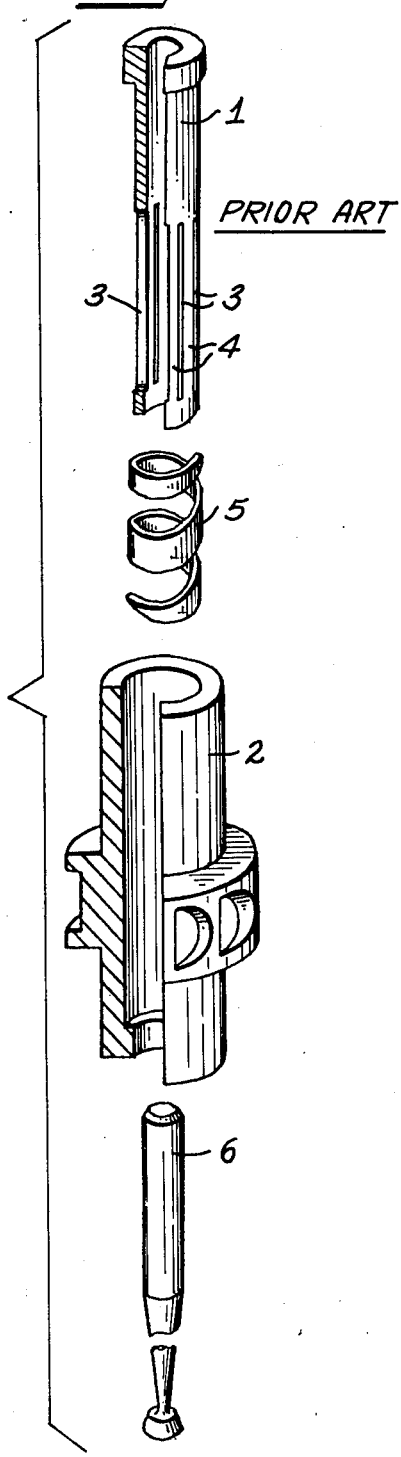
FIGS. 1 and 2 are illustrations of prior art proposals.

Referring first to FIG. 1, a prior proposal provided a tubular member 1 to be inserted in a dental handpiece turbine 2. The sleeve was provided with slits 3 defining resilient strips 4, the slit portion of the sleeve was surrounded by a helical spring 5 arranged to exert radially inward pressure. Thus, the strips 4 were bowed inwardly to exert frictional grip on the shank 6 of a dental drill when inserted axially in the device.

Figure 2:
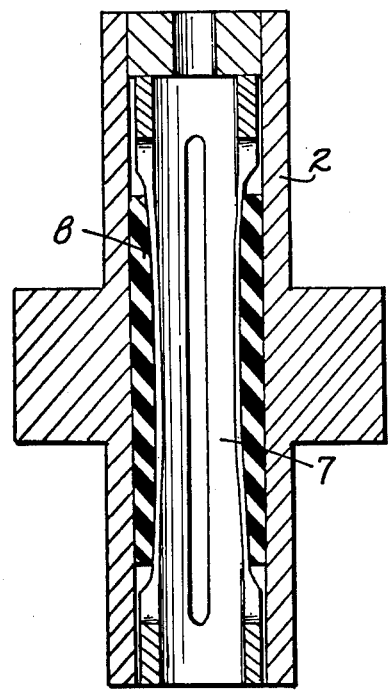

A second prior proposal is illustrated in FIG. 2 wherein a rotor 2 is provided with a split sleeve 7, like that of FIG. 1, and a sleeve or tube 8 of rubber or the like is positioned between the sleeve 7 and the bore of the rotor 2 to bow the sleeve inwardly as illustrated, to effect a frictional grip on the shank of a dental drill. As pointed out previously, however, the proposals of both FIGS. 1 and 2 result in exerting holding pressure on the dental drill only in a central region thereof which resulted in excessive wear and difficulty in inserting the dental drill.

In the form of the present invention illustrated generally in FIG. 3, a sleeve 10 is provided having a bore 12 therethrough, the bore 12 being slightly larger in diameter than the outer diameter of a helical spring 13. A plug member 14 is threadedly received in the lower end of the sleeve 10 and defines an upwardly facing annular abutment surface 15 which bears against the lower end of spring 13 when the latter is placed in the sleeve. The upper end of spring 13 is provided with a notched portion 16 and an upper retainer plug 17 is positioned in the upper end of sleeve 10. The plug 17 is provided with a bore 18 therethrough and a cutaway portion 19 complementary to the cutaway portion or notch 16 of the spring 13. Thus, when the parts are assembled as shown in section in FIG. 4, and mounted in turbine rotor 2, the plug abuts the upper end of the spring 13 and the cutaway portions of both nest together as shown to provide driving torque from turbine 2, through sleeve 10 to the spring 13.

The spring 13 is so dimensioned that its inner diameter, when relaxed, is slightly less than the diameter of the shank 6 of a drill to be held therein. Thus, when the drill shank is pushed upwardly, through the opening in lower plug 14, it engages the lower end of the spring 13 and continued force compresses that spring in an axial direction. Such axial compression results in outward radial expansion of the spring sufficient to increase its inner diameter to a point where it can slidably receive the shank of the drill. Thus, the drill may be inserted by simple axial pressure with a relatively light force. As the turbine rotates in the direction of the arrow 20 of FIG. 3, the spring 13 acts as a friction clutch gripping the drill shank throughout its entire length to effect drive thereof.

When it is desired to remove the drill from the holder, any suitable rod, pin or similar tool may be pushed downwardly through opening 18 in upper plug 17 and it engages the end of the drill shank. Downward pressure on the drill shank, acting through friction between the drill shank and the spring 13 causes the spring to compress downwardly, such movement of its upper end being permitted by its axially slidable engagement with the upper plug 17. Such downward compression of the spring enlarges its diameter and permits the drill to be freely and readily pushed from the holder by the tool or pin being used.

FIG. 5 shows a second embodiment of the invention and illustrates the entire assembly in the handpiece 21 of a dental drill wherein the turbine 2 is mounted in bearings 22 in the usual manner. All parts in FIG. 5 bearing the same reference numerals as those parts in FIGS. 3 and 4 are identical thereto. In this form of the invention, however, an upper plug member 23 engages the upper end of the spring 13 in the same manner as previously described. However, the plug 23 is provided with a key groove 24 engaging a key pin 25 on the sleeve 10 and the plug 23 is vertically slidable in the sleeve 10 but is keyed against rotation therein. A manually depressible button 26 is provided on the handpiece 21 overlying the plug 23. A compression spring 27 urges the button 26 outwardly.

To insert a drill in the form shown in FIG. 5, it is only necessary to push the drill shank upwardly through bottom plug 14, thus compressing the spring 13 and enlarging the same, as described with reference to FIGS. 3 and 4.

When it is desired to remove the drill from the holder, the button 26 may be manually pushed downwardly with sufficient force to overcome the force of spring 27 and until the button engages the plug 23.

Further, downward movement of the button will cause the plug 23 to slide downwardly in sleeve 10 and since that plug abuts the upper end of spring 13 such downward movement will cause the spring to be compressed axially with its attendant radial expansion and release of the frictionally gripped shank.

While a limited number of specific embodiments of the invention have been shown and described herein, the same are merely illustrative of the principles involved and other embodiments may be resorted to within the scope of the appended claims.

I claim:

1. In a dental handpiece having a rotor provided with an axial bore therein:

a helical spring in said bore, of an outer diameter slightly less than the diameter of said bore and having an inner diameter slightly less than that of the shank of a drill to be frictionally held and driven thereby;

driving means drivingly connecting one end of said spring to said rotor;

release means for selectively axially compressing said spring to thereby radially expand the same to release the shank of a drill therein;

said driving means comprising a top abutment member at one end of said spring having a notch drivingly receiving an end of said spring but permitting relative axial movement therebetween; and said release means including an annular bottom abutment fixed in said bore and engaging the other end of said spring and an opening through said top abutment member for insertion of a tool to engage a drill frictionally held in said spring and thereby axially compress said spring against said annular abutment.

2. A device as defined in claim 1 wherein said annular abutment comprises a member releasably threaded into one end of said bore.

3. In a dental handpiece device having a rotor provided with an axial bore therein:

a helical spring in said bore, of an outer diameter slightly less than the diameter of said bore and having an inner diameter slightly less than that of the shank of a drill to be frictionally held and driven thereby;

driving means drivingly connecting one end of said spring to said rotor;

release means for selectively axially compressing said spring to thereby radially expand the same to release the shank of a drill; and an annular abutment in said bore engaging the other end of said spring; said first abutment being drivingly keyed in said bore but axially slidable therein to effect compression of said spring against said annular abutment.

4. A device as defined in claim 3 including an actuator for applying pressure to said first abutment to effect sliding thereof in said bore, and spring means urging said actuator away from said first abutment.

* * * * *